United States Patent [19]

Debourge et al.

[11] 4,049,801

[45] Sept. 20, 1977

[54] PHOSPHITE COMPOUNDS AS FUNGICIDAL AGENTS

[75] Inventors: Jean-Claude Debourge, Lyon;
Jean-Michel Gaulliard, Orlienas;
Jean Pierre Thiolliere, Lyon; Jean
Georges Abblard, Caluire;
Guy-Bernard Lacroix, Lyon; Daniel
Jean Pillon, Lyon; Jacques Joseph
Ducret, Lyon; Andre Thizy, Lyon, all
of France

[73] Assignee: Philagro, France

[21] Appl. No.: 613,877

[22] Filed: Sept. 16, 1975

Related U.S. Application Data

[62] Division of Ser. No. 432,492, Jan. 11, 1974, Pat. No. 3,968,208.

[30] Foreign Application Priority Data

Jan. 12, 1973  France ............................... 73.01803
Oct. 19, 1973  France ............................... 73.37994

[51] Int. Cl.² ............................................. A01N 9/36
[52] U.S. Cl. ................................... 424/217; 424/199;
424/273 R; 424/274; 424/300; 424/DIG. 8
[58] Field of Search ................. 424/DIG. 8, 199, 217;
260/953

[56] References Cited

U.S. PATENT DOCUMENTS 3,591,682  7/1971  Thiolliere ..................... 424/217 X

OTHER PUBLICATIONS

Lucas et al., Journ. Amer. Chem. Soc. 1950, vol. 72, pp. 5491-5497.
Oswald, Can. Chem., vol. 37, pp. 1498-1504 (1959).
Zwierzak, Can. J. Chem. 45 (21), pp. 2501-2512 (1967).
Chemical Week, June 21, 1972, 5 pages.

*Primary Examiner*—Allen J. Robinson
*Attorney, Agent, or Firm*—Robert E. Burns; Emmanuel J. Lobato; Bruce L. Adams

[57] ABSTRACT

Fungicidal compositions for controlling fungus diseases in plants are disclosed. These compositions contain as their active materials compounds and polymers thereof corresponding to the formula:

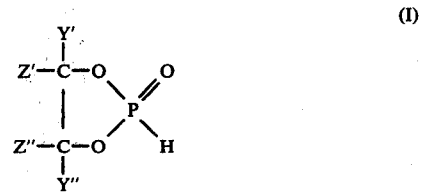

(I)

in which Y', Y'', Z' and Z'' represent a hydrogen atom or an optionally halogenated alkyl radical containing from 1 to 5 carbon atoms. Included within these active materials are the hydrolysates, salts and quaternary salts of these phospholanes. These cyclic phospholanes or phosphites and their hydrolysates are compatible with other commercial fungicides and the compositions disclosed include these compounds above and in combination with such other fungicides.

10 Claims, No Drawings

PHOSPHITE COMPOUNDS AS FUNGICIDAL AGENTS

This is a divisional of application Ser. No. 432,492, filed Jan. 11, 1974, now U.S. Pat. No. 3,968,208 issued July 6, 1976.

FIELD OF THE INVENTION

This invention relates to fungicidal compositions based on cyclic phosphites.

THE INVENTION

More particularly, the invention relates to compositions suitable for use in controlling parasitic fungi in plants and containing as active material at least one compound corresponding to the formula:

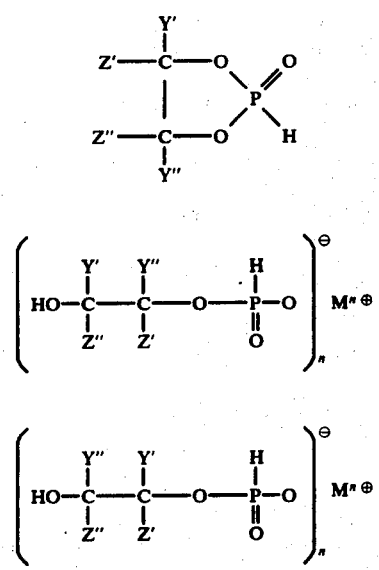

in which Y', Y''', Z' and Z'' represent a hydrogen atom or an optionally halogenated alkyl radical containing from 1 to 5 carbon atoms, M represents an atom of hydrogen, metal or an ammonium or mono, di, or tri (hydroxyl) alkyl ammonium radicals and $n$ is an integer equal to the valency of M. Suitable metals include alkali and alkaline-earth metals, such as sodium, potassium, barium, magnesium, calcium, or such metals as iron, copper, zinc, manganese, nickel, cobalt or mercury.

The invention also relates to fungicidal compositions suitable for use in controlling mildew in the vine (*Plasmopara viticola*), tobacco (*Peronospora tabacina*) and hops (*Pseudoperonospora humili*), containing as active material a mixture of two or more compounds corresponding to formulae (I), (IIA), and (IIB) abo above.

DETAILED DESCRIPTION

These compounds are known per se. A certain number of methods by which they can be synthesised can be found in the literature.

The cyclic derivatives of formula I can be prepared for example by the following process carried out in two stages: in the first stage, an anhydrous α-glycol is reacted with anhydrous phosphorus trichloride in solution in dichloromethane to form a cyclic glycol chlorophosphite in accordance with the following reaction scheme:

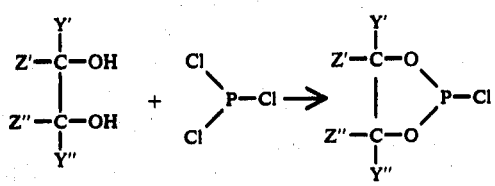

Since this reaction is highly exothermic, the reaction mixture has to be cooled. The solvent is eliminated by distillation after about 1.5 hours, the resulting product being distilled under reduced pressure.

In a second stage, the chlorophosphite in solution in dioxan is hydrolysed by the addition of water in accordance with the following reaction:

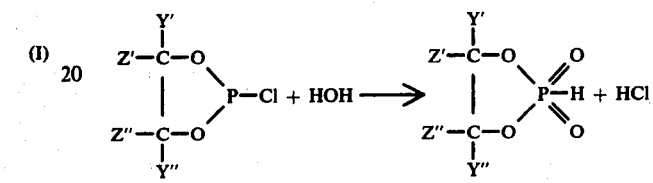

The evolution of hydrochloric acid is promoted by maintaining a temperature around ambient temperature and a reduced pressure.

It is also possible to obtain the same compounds by transesterifying diethylphosphite in the presence of an α-glycol (OSWALD, Can. Chem. Vol. 37, page 1498).

Unfortunately, the products obtained by these two methods contain not only the cyclic derivative, but also more viscous derivatives.

One method of obtaining the cyclic product is to hydrolyse the cyclic chlorine-containing derivative with a stoichiometric quantity of water in the presence of a hydrochloric acid acceptor.

It is known (cf. Journ. Amer. Chem. Soc. 1950, page 5491) that certain cyclic phosphonates corresponding to the above formulae in which Y' and Y'' are hydrogen whilst Z' and Z'' represent hydrogen on the one hand and a methyl on the other hand, or both represent hydrogen or a methyl, are readily soluble in water and give a neutral solution which gradually acidifies due presumably to hydrolysis into monohydroxyalkyl phosphite. In other words, when the cyclic compounds of formula I are in contact with water, there is an equilibrium between the cyclic form and the form resulting from opening of the ring by hydrolysis. In practice, an aqueous composition of one of the cyclic derivatives contains a mixture of both forms. This reaction is more complete in alkaline medium.

We have found that the cyclic compounds of formula I, irrespective of whether they have been obtained by one or other of the methods described above, undergo ring-opening in aqueous medium to form at least partly linear compounds corresponding to formulae IIA and IIB. In addition, analysis has shown that the viscous products referred to above are oligomers of compounds corresponding to formulae IIA and IIB. These oligomers are also present in compositions based on cyclic compounds which have been stored.

This explains why the fungicidal compositions according to the invention can contain active materials corresponding to the different formulae. Thus, if the starting product is cyclic compound of formula (I), this compound, on being dissolved in water or in a medium containing water, or even if it is merely in contact with water, is progressively partially hydrolysed to give linear compounds of formulae (IIA) and (IIB), the composition ultimately used being formed by a mixture more or less rich in one or other of the different structures, each of which has similar fungicidal properties.

The compounds of general formulae IIA and IIB can thus be prepared by the preferably alkaline hydrolysis of corresponding cyclic derivatives. They can also be obtained by known methods for preparing monoesters of phosphorous acid for example (Journal of the Chemical Faculty of the Russian Chemical Academy, 1972, Vol. 42, page 1930) by dealkylating the corresponding diesters with metal halides in accordance with the following reaction:

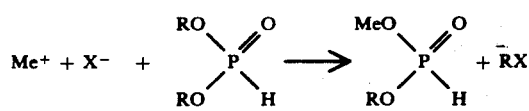

The same result can also be obtained by treating a dialkyl phosphite with a base (soda or ammonia). In this case (cf. Journ. Org. Chem. 1962, page 2521), the aforementioned ammonium salt is obtained.

We have also found that, during storage, the compounds according to the invention show a tendency towards condensation to form much more viscous oligomers. These compounds in turn readily give the active compounds of formulae IIA and IIB by dissolution in water or by contact with water, as explained above.

The following compounds have been obtained by the above methods:

2-hydroxy-4-methyl-1,3,2-dioxaphospholane,
2-hydroxy-4-chloromethyl-1,3,2-dioxaphospholane,
2-hydroxy-1,3,2-dioxaphospholane,
2-hydroxy-4,5-dimethyl-1,3,2-dioxaphospholane
0-(2-hydroxypropyl)-phosphite
0-[(1-methyl-2-hydroxy)-ethyl]-phosphite
sodium 0-(2-hydroxypropyl)-phosphite
ammonium 0-(2-hydroxypropyl)-phosphite
monoethanolamine 0-(2-hydroxypropyl)-phosphite
calcium 0-(2-hydroxypropyl)-phosphite
barium 0-(2-hydroxypropyl)-phosphite
0-(2-hydroxy-3-chloropropyl)-phosphite
0-(1-chloromethyl-2-hydroxyethyl)-phosphite
0-(2-hydroxyethyl)-phosphite
0-(1,1-dimethyl-2-hydroxyethyl)-phosphite
0-(1-methyl-2-hydroxypropyl)-phosphite
sodium 0-(methyl 2-hydroxyethyl) phosphite
ammonium 0-(1-methyl-2-hydroxyethyl) phosphite
ethanolammonium 0-(1-methyl 2-hydroxyethyl) phosphite
diethylammonium 0-(2-hydroxypropyl) phosphite
diethylammonium 0 (1-methyl 2-hydroxyethyl) phosphite
diemethylammonium 0-(2-hydroxyethyl) phosphite
diethylammonium 0-(2-hydroxethyl) phosphite
diisopropylammonium 0- (2-hydroxyethyl) phosphite The following Examples illustrate the preparation and use of the compounds according to the invention.

EXAMPLE 1

Preparation of 2-hydroxy-4-methyl-1,3,2-dioxaphospholane, 0-(2-hydroxypropyl)-phosphonate and 0-(1-methyl-2-hydroxy-ethyl)-phosphonate (compound Nos. 1, 5 and 6).

A. In a first method, 4-methyl-2-oxo-2H-1,3,2-dioxaphospholane is synthesised by hydrolysing 4-methyl-2-chloro-1,3,2-dioxaphospholane in the presence of a hydrochloric acid acceptor, such as pyridine, in accordance with the following reaction:

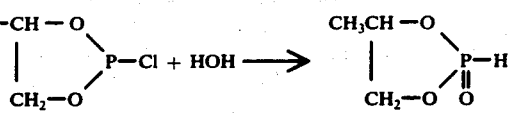

28.1 g (0.2 mole) of chlorophosphite are dissolved in 250 ml of anhydrous toluene and the resulting solution cooled while stirring to below 15° C. This is followed by the gradual introduction of 3.6 g (0.2 mole) of water in solution in 15.8 g (0.2 mole) of anhydrous pyridine.

On completion of the addition, the temperature of the reactants is allowed to rise to 20° C. The pyridine hydrochloride is filtered and the toluene removed in vacuo.

The residue, in the form of a fluid oil, is distilled in vacuo.

| Yield: | 57% |
|---|---|
| boiling point: | 64° C/0.1 mm Hg |
| $n_D^{20}$ = 1.472 | |

This mobile liquid which has a geranium odor is soluble in all organic solvents. The NMR spectrum indicates that the product (compound 1) is a mixture of 2 isomers of cyclic form.

| Analysis for $C_3H_7O_3P$: | | | |
|---|---|---|---|
| Elemental analysis | C% | H% | P% |
| Calculated | 29.50 | 5.74 | 25.40 |
| Found | 29.33 | 6.13 | 25.48 |

The product is then dissolved in acetonitrile and one equivalent of water added to the resulting solution. Removal of the solvent leaves a liquid product ($n_D^{20}$ = 1.4528) containing 97% of a mixture of the following compounds:

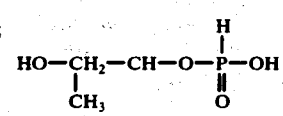

and

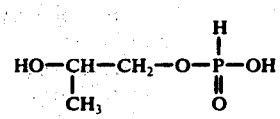

Centesimal analysis for $C_3H_9O_4P$

| Analysis | C % | H % | P % |
|---|---|---|---|
| Calculated | 25.71 | 6.43 | 22.14 |

| Found | 25.76 | 6.18 | 22.17 |

B. In another method, 1 mole of anhydrous 1,2-propyleneglycol is reacted with 1 mole of anhydrous phosphorus trichloride in solution in dibromomethane. The chloro-phoshite of propylene glycol is quantitatively obtained in accordance with the following reaction:

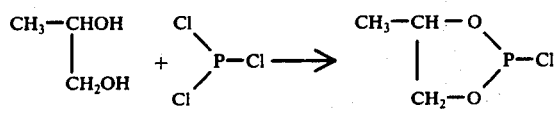

Since the reaction is exothermic, the reaction mixture is cooled. After about 1.5 hours, the solvent is removed by distillation and the resulting product distilled under reduced pressure. This is followed by the addition of two equivalents of water to one equivalent of chlorophosphite in solution in acetonitrile.

C. The method described by OSWALD (J.Can. Chem. Vol. 37, page 1498) is used with diethylphosphite and propylene glycol in accordance with the following scheme:

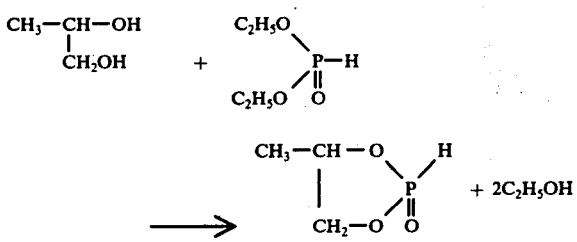

A mixture of 1 mole of each of the reactants is heated to 120°–130° C under a pressure of 120 mmHg until distillation of the glycol has stopped, which takes about 3 hours.

The distilled product, obtained in a yield of 71%, is a colourless viscous oil with an index $n_D^{20}$ of 1.469 and a boiling point of 106°–107° C/10$^{-3}$ mmHg.

This oil is soluble in water, alcohol, acetone, and insoluble in aromatic solvents.

| Analysis for $C_3H_7O_3P$ | | | |
|---|---|---|---|
| Analysis | C % | H % | P% |
| Calculated | 29.50 | 5.74 | 25.40 |
| Found | 30.69 | 6.24 | 22.46 |

The corresponding open derivatives are obtained in the same way as described above in A).

D) The method adopted is the method described by Mandelbaum et al in C.A. 69, 43338h (1968) for the production of dialkylphosphites, comprising reacting phosphorus trichloride with a mixture of propylene glycol and methanol at a temperature below −15° C. Removal in vacuo of the hydrochloric acid and methylene chloride leaves compound 1 whose structure is confirmed by infra-red spectrum.

Compounds 5 and 5 can be obtained from compound 1 as described above in A).

EXAMPLE 2

Preparation of sodium 0-(2-hydroxypropyl)-phosphite (compound No. 7)

The 0-(2-hydroxypropyl)-phosphite obtained in Example 1 is neutralised and dissolved in water by the addition of normal caustic soda. A vitreous, highly hygroscopic product is obtained by precipitation.

| Centesimal analysis for $C_3H_8NaO_4P$ | | | |
|---|---|---|---|
| Analysis | C % | H % | P % |
| Calculated | 22,22 | 4,94 | 13,66 |
| Found | 21,83 | 5,11 | 13,77 |

EXAMPLE 3

Preparation of ammonium 0-(2-hydroxypropyl)-phosphite (compound No. 8)

The procedure is as described above, except that the soda is replaced by ammonia. A vitreous, highly hygroscopic product is obtained by precipitation.

| Centesimal analysis for $C_3H_{12}NO_4P$ | | | |
|---|---|---|---|
| Analysis | C% | H% | N% | P% |
| Calculated | 22,93 | 7,64 | 8,92 | 19,75 |
| Found | 22,88 | 7,93 | 8,82 | 19,52 |

EXAMPLE 4

Preparation of the ethanolamine salt of 0-(2-hydroxypropyl)-phosphite (compound No. 9)

The procedure is as in Example 2, except that the soda is replaced by monoethanolamine. A vitreous, highly hygroscopic product is obtained by precipitation.

EXAMPLE 5

Calcium and barium salts of 0-(2-hydroxypropyl)-phosphite (compounds Nos 10 and 11)

The procedure is as in Example 2 except that the soda is replaced by calcium hydroxide and barium hydroxide, respectively. The corresponding salts are obtained.

EXAMPLE 6

Preparation of 0-(2-hydroxy-3-chloropropyl)-phosphite and of 0-(1-chloromethyl)-2-hydroxyethyl phosphite (compounds Nos 12 and 13)

Following the procedure of Example 1, method B), 4-chloromethyl-2-chloro-1,3,2-dioxaphospholane is hydrolysed in solution in methylene chloride with two equivalents of water. The liquid obtained, of index $n_D^{20}$ = 1.5008, contains approximately 93% of a mixture of the following two isomeric compounds:

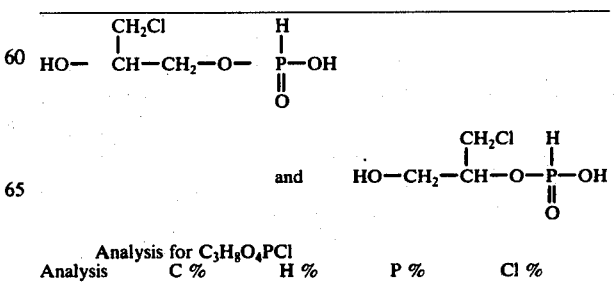

| Analysis for $C_3H_8O_4PCl$ | | | |
|---|---|---|---|
| Analysis | C % | H % | P % | Cl % |

| | | | | |
|---|---|---|---|---|
| Calculated | 20.63 | 4.58 | 17.77 | 20.34 |
| Found | 20.58 | 4.94 | 17.66 | 20.18 |

The structure of the two compounds is confirmed by the NMR-spectrum.

EXAMPLE 7

Preparation of 0-(2-hydroxyethyl)-phosphite (compound No 14)

2-Chloro-2,3,2-dioxapholane is hydrolysed in the same way as described in Example 1, method B), giving a liquid which is soluble in water and which contains the required product, as shown by the NMR-spectrum.

EXAMPLE 8

Preparation of diethylammonium salts of 0-(2-hydroxy propyl) phosphite (compound No 20) and 0-(1-methyl 2-hydroxy ethyl) phosphite (compound No 21).

The procedure is as described above in example 2, except that the soda is replaced by diethylamine. A liquid ($n_D^{20} = 1,452$) is obtained by precipitation with a quantitative yield.

Centesimal analysis for $C_7H_{20}NO_4P$

| Analysis | C% | H% | N% | P% |
|---|---|---|---|---|
| Calculated | 39,4 | 9,38 | 6,57 | 14,55 |
| Found | 39,49 | 9,11 | 6,56 | 14,70 |

Practically a mixture of the salts of the two isomers is obtained.

EXAMPLE 9

Preparation of salts of respectively dimethyl-diethyl-, and diisopropylammonium of 0-(2-hydroxy-ethyl) phosphite (compounds No 22, 23 and 24)

The procedure is as described in example 2, except that the soda is respectively replaced by dimethyl), diethyl-, and diisopropylamine. The final products are liquids which are obtained with a quantitative yield.

| Compound | Molecular | ref. index $n_D^{20}$ | Centesimal analysis | Calcul. | Found |
|---|---|---|---|---|---|
| 22 | $C_4H_{14}NO_4P$ | 1,458 | C% | 28,25 | 27,65 |
|  |  |  | H% | 8,18 | 8,11 |
|  |  |  | N% | 8,18 | 7,78 |
|  |  |  | P% | 18,13 | 18,34 |
| 23 | $C_6H_{18}NO_4P$ | 1,458 | C% | 36,18 | 36,41 |
|  |  |  | H% | 9,05 | 9,15 |
|  |  |  | N% | 7,04 | 7,12 |
|  |  |  | P% | 15,58 | 15,63 |
| 24 | $C_8H_{22}NO_4P$ | 1,4625 | C% | 42,3 | 42,16 |
|  |  |  | H% | 9,7 | 10,04 |
|  |  |  | N | 6,17 | 6,20 |
|  |  |  | P | 13,66 | 13,77 |

EXAMPLE 10

In vitro test on mycelian growth

The products according to the invention are tested for their effect on the mycelian growth of the following fungi:

*Rhizoctonia solani*, responsible for canker of the neck,
*Fusarium oxysporum*, responsible for tracheomycosis,
*Fusarium nivale*, responsible for damping-off of seedlings of cereal crops,
*Fusarium roseum*, responsible for fusariosis in cereal crops,
*Sclerotinia minor*, responsible for sclerotiniosis,
*Sclerotinia sclerotiorum*, responsible for sclerotiniosis,
*Pythium de Baryanum*, responsible for damping-off of seedlings,
*Phomopsis viticola*, responsible for black rot,
*Septoria nodorum*, responsible for septoriosis in cereal crops,
*Helminthosporium*, responsible for helminthosporiosis,
*Verticillium*, responsible for verticilliosis,
*Cercospora beticola*, responsible for cercosporiosis,
*Gloesporium perennans*, responsible for the rotting of apples in storage.

The "Agar Plate Dilution" method is used for each test. A mixture of gelose and an acetone solution or a wettable powder containing the material to be tested in a concentration of 0.25 g/l, is poured into a Petri dish at a temperature of around 50° C.

The wettable powder is prepared by mixing the following ingredients for 1 minute in a cutter mill:

| | |
|---|---|
| active material to be tested | 20% |
| deflocculant (calcium lignosulphate) | 5% |
| wetting agent (sodium alkylaryl sulphate) | 1% |
| filler (aluminium silicate) | 74% |

This wettable powder is then mixed with a quantity of water for a single application in the required dose.

The gelose-containing mixture is allowed to solidify and discs of mycelian culture of the fungus placed on it.

A Petri dish similar to the other Petri dish, except that the gelose medium does not contain active material, is used as control.

After 4 days at 20° C, the surface area of the inhibition zone observed is evaluated and expressed as a percentage of the inoculated surface area.

| | % inhibition | |
|---|---|---|
| Fungus | Product No. 1 | Product No. 2 |
| Rhizoctonia | 50 | 50 |
| Fusarium oxysporum | 60 | 60 |
| Fusarium nivale | 78 | 65 |
| Fusarium roseum | 60 | 70 |
| Sclerotinia minor | 83 | 100 |
| Sclerotinia sclerotiorum | — | 50 |
| Pythium | 100 | 100 |
| Phomopsis | 50 | 50 |
| Septoria | 95 | 70 |
| Helminthosporium | 83 | 70 |
| Verticillium | 100 | 100 |
| Cercospora | — | 90 |
| Gloesporium | 60 | — |

EXAMPLE 11

In vivo test on ground fungus

The products according to the invention are tested for their action on *Pythium de Baryanum* in cucumbers.

The following procedure is adopted for each test: a medium containing a culture of the fungus is mixed with a sterilised earth and pots filled with the resulting mixture. After 8 days, the earth is infested. It is then treated by spraying with a suspension of the active material to be tested in various concentrations. The active material is in the form of a wettable powder prepared as described in Example 1.

Cucumber seeds are then sown in the treated soils.

The results of the test are assessed 15 days after sowing of the seeds by counting the number of destroyed or sick plants in relation to an untreated control and a non-contaminated control.

Under these conditions, products 1 and 2 afford complete protection in a dose of 0.5 g/l.

EXAMPLE 12

In vivo test on living organs:

Test on tomato mildew, *Phytophora infestans*

One drop of a mixture of a suspension of spores containing approximately 80,000 units per cc, and of a suspension in the required dilution of a wettable powder of the same composition as that described in Example 8, in the case of an insoluble product, or of an acetone solution, is applied to freshly cut tomato leaves.

Under these conditions, product 1 and 2 afford complete protection in a dose of 0.5 g/l, whilst product 1 affords adequate protection in a dose of 0.125 g/l.

EXAMPLE 13

In vivo test on *Plasmopara viticola* in plants a. preventive treatment

Pot-grown vine plants are treated by spraying the underneath of their leaves with an aqueous suspension of a wettable powder having the following composition by weight:

| active material to be tested | 20% |
| deflocculant (calcium lignosulphate) | 5% |
| wetting agent (sodium alkylaryl sulphonate) | 1% |
| filler (aluminium silicate) | 74% | in the required dilution containing the active material to be tested in the appropriate dose. Each test is repeated twice.

After 48 hours, the plants are infected by spraying the underneath of their leaves with an aqueous suspension containing approximately 80,000 units per cc of spores of the selected fungus.

The pots are then placed for 48 hours in an incubation cell at 20° C/100% relative humidity.

The plants are inspected 9 days after infestation.

Under these conditions, compounds 1, 2, 3 and 5 to 16 afford complete protection in a dose of 0.5 g, compounds 5 to 23 also afford complete protection in a dose of only 0.25 g/l, whilst the cyclic compound, compound No. 1, has a distinctly inadequate effect.

In addition, none of the products tested showed the least sign of phytotoxicity.

b. systemic test by root absorption on vine mildew

The base of several vine stocks (Gamay veriety) each accomodated in a pot containing vermiculite and a nutritive solution, are sprayed with 40 cc of a solution containing 0.1 g/l of the material to be tested. After 2 days, the vine is contaminated with an aqueous suspension containing 100,000 spores per cc of *Plasmopara viticola*. The vine thus treated is left to incubate for 48 hours in a room at 20° C/100% relative humidity. The degree of infestation is observed after about 7 days in relation to an infested control sprayed with 40 cc of distilled water.

Under these conditions, compounds 1 and 5 to 23 absorbed by the roots provide the vine leaves with complete protection against mildew, which clearly demonstrates the systemic character of these compounds.

c. systemic test by foliar absorption on vine mildew

Several vine stocks (Gamay variety), each accommodated in a pot containing a mixture of pure earth and sand, are treated at the stage of 7 leaves by spraying a wettable powder containing 1 g/l of the active material to be tested onto the underneath of the 4 lowest leaves. This is followed by incubation for 48 hours in a room at 20° C/100% relative humidity. The degree of infestation is noted after about 7 days on the fifth to seventh leaves, counting from the bottom upwards, in relation to a control which has been treated with distilled water.

Under these conditions, compounds Nos 1 and 5 to 23 provide the uppermost leaves of the vine with complete protection against mildew. The systemic effect observed in the preceding Example is confirmed when the active material is applied to leaves.

EXAMPLE 14

Open-air test on vine mildew

Groups of vine stocks (Gamay) are naturally infested at the beginning of the month of August, following abundant rainfall and frequent watering. These groups of vine stocks are then treated after 8, 14 and 23 days, respectively, with 50% "slurries" of wettable powders respectively containing as active material compound No 1, manganese ethylene-1,2-bis-dithiocarbamate, or manebe, and a mixture of these two compounds.

The following Table shows the results of observations made 2, 8, 20, 35 and 45 days, respectively, after the final treatment. These results are expressed in percentage protection in relation to a contaminated, but untreated control.

| Active material | Dose g/l | Observation after | | | | |
| --- | --- | --- | --- | --- | --- | --- |
| | | 2 days | 8 days | 20 days | 35 days | 45 days |
| Compound No. 1 | 2 | 100 | 70 | 15 | 10 | 0 |
| maneb | 1.2 | 95 | 93 | 88 | 77 | 70 |
| compound No. 1 | 2 + 1.2 | 100 | 100 | 100 | 95 | 90 |

This Table clearly illustrates, on the one hand, the excellent immediate action of compound No. 1, on the other hand the remarkable persistence of the mixture, which is greater than that of maneb used on its own, and finally the absence of phytotoxicity of compound No 1 on vine.

EXAMPLE 15

Several groups of 10 vine stocks (Gamay variety) are subjected from spring to the beginning of August to regular, very fine spraying so as to produce heavy contamination with mildew. The groups of vine stocks are treated respectively with a known fungicide (manganese dithiocarbamate, or maneb, and N-(trichloromethylthio)-phthalimide) used in the standard dose, and with compound No 5. At the end of August, the percentage of leaves affected by mildew is counted for each group.

| Active material | Dose in g/hl | % of sick leaves |
| --- | --- | --- |
| Compound No 5 | 300 | 1.8 |
| maneb | 280 | 4.3 |
| folpet | 150 | 25 |
| control | — | 90 |

This Table clearly illustrates the superiority of the compounds according to the invention over known anti-mildew fungicides. It should be noted that results similar to those produced by compound No 5 are obtained with compound No 1 of the Parent Patent.

EXAMPLE 16

Several groups of 10 vine stocks (Gamay variety) are treated against mildew (plasmopara vitricola) from spring to the beginning of August (10 treatments) with a 50% wettable powder (unless indicated otherwise) containing known fungicides (copper oxychloride, maneb, folpet, N-(trichloromethylthio)-3a, 4, 7, 7a-tetrahydro-phthalimide or captan and N-(1,1,2,2-tetrachloroethylthio)-3a, 4, 7, 7a-tetrahydrophthalimide or captafol) in the standard dose, on the one hand alone and, on the other hand with a dose 2 to 3 times lower in admixture with 300 g/hl of compound No 5. Protection is observed on the 31st of August and then on the September 27th. The following Table shows the results expressed as a percentage of the surface area of the patches of mildew in relation to the total surface area of the leaves.

| Known fungicide | + compound | % of the surface area of the leaves protected | |
|---|---|---|---|
| | | 31/8 | 27/9 |
| Copper oxychloride | | | |
| 500 | — | 90 | 90 |
| 120 | — | 80 | 60 |
| 120 | 300 | 100 | 95 |
| Maneb | | | |
| 280 | — | 95 | 95 |
| 120 | — | 70 | 70 |
| 120 | 300 | 97.5 | 90 |
| Captan | | | |
| 175 | — | 85 | 70 |
| 70 | — | 70 | 40 |
| 70 | 300 | 96.5 | 70 |
| Captafol | | | |
| 160 | — | 85 | 85 |
| 70 | — | 70 | 70 |
| 70 | 300 | 100 | 95 |
| Folpet | | | |
| 150 | — | 85 | 85 |
| 70 | — | 70 | 60 |
| 70 | 300 | 97.5 | 85 |

These results clearly demonstrate the remarkable ability of the compounds according to the invention to afford, in combination with low doses of known fungicides, distinctly better protection than that afforded by these fungicides used in the standard dose.

It should also be noted that, when used under the same conditions as compound No 5, compound No 1 gives similar results.

Finally, tests on tobacco and hops have shown that compounds Nos 1 and 5 are active in protecting these plants against mildew without any signs of phytotoxicity.

These Examples clearly demonstrate the remarkable fungicidal properties of the compounds according to the invention, namely the wide spectrum comprising ground fungi and mildews, and in their case, an immediate, systemic and inhibiting action and the absence of phytotoxicity on vine.

Accordingly, the compounds according to the invention can be used generally for protecting plants against fungus disease and, more particularly, the vine against mildew, both in preventive and in curative treatment. They can be used either on their own or in admixture with one another and, in particular, with cyclic compounds of formula I and open compounds corresponding to formulae IIA and IIB, and in association with known fungicides such as metallic dithiocarbamates (maneb, zineb, mancozeb), basic salts or hydroxides of copper, (tetrahydro)-phthalimides (captan, captafol, folpet), methyl N-(1-butyl-carbamoyl)-2-benzimidazole carbamate (benomyl), methyl N-2-benzimidazole carbamate, etc., either in order to complete the spectrum of activity of the compounds according to the invention or to increase their persistence.

By virtue of these properties, the compounds according to the invention can be used for protecting plants against fungus disease, more especially in agriculture, arboiculture, horticulture, market gardening and, more particularly, in viticulture, and for the treatment of seeds.

For practical application, the compounds according to the invention are rarely used on their own. More often they form part of formulations generally comprising a support and/or a surfactant in addition to the active material according to the invention.

In the context of the invention, a support is an organic or mineral, natural or synthetic material with which the active material is associated to facilitate its application to the plant, to seeds or to the soil, or its transportation or handling. The support can be solid (clays, natural or synthetic silicates, resins, waxes, solid fertilisers ....) or fluid (water, alcohol, ketones, petroleum fractions, chlorinated hydrocarbons, liquefied gases).

The surfactant can be an ionic or non-ionic emulsifier, dispersant or wetting agent such as, for example, salts of polyacrylic acids, lignin-sulphonic acids, condensates of ethylene oxide with fatty alcohols, fatty acids or fatty amines.

The compositions according to the invention can be prepared in the form of wettable powders, dusting powders, granulates, solutions, emulsified concentrates, emulsions, suspended concentrates and aerosols.

The wettable powders are normally prepared in such a way that they contain from 20 to 85% by weight of active material. In addition to a solid support, they normally contain from 0 to 5% by weight of a wetting agent, from 3 to 10% by weight of a dispersant and, when necessary, from 0 to 10% by weight of one or more stabilisers and/or other additives, such as penetration agents, adhesives or anti-lumping agents, colourants, etc. For example, a wettable powder can have the following composition:

| | |
|---|---|
| active material | 50% |
| calcium lignosulphate (deflocculant) | 5% |
| anionic wetting agent | 1% |
| anti-lumping silica | 5% |
| kaolin (filler) | 39% |

Aqueous dispersions and emulsions, for example compositions obtained by diluting with water a wettable powder or an emulsifiable concentrate such as described above, are included within the general scope of the invention. These aqueous compositions are of considerable practical significance. Due to the hydrolysis reactions of the compounds of formula I, the preparation of compositions of this kind spontaneously produces corresponding compounds IIA and IIB so that the compositions often contain a mixture of the two types of compounds. These emulsions can also be of the water-in-oil type or of the oil-in-water type and they can have a thick consistency resembling that of a mayonnaise.

The compositions according to the invention can contain other ingredients, for example protective colloids, adhesives or thickeners, thixotropic agents, stabilisers or sequestrants, and other active materials known to have pesticidal properties, in particular acaricides or insecticides.

We claim:

1. A fungicidal composition for controlling fungus disease in plants containing a fungicidally effective amount of at least one compound corresponding to the formula;

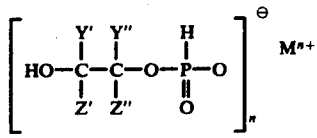
(II)

in which Y', Y'', Z' and Z'' are the same or different and are selected from the group consisting of hydrogen, alkyl of from 1 to 5 carbon atoms an halogenated alkyl of from 1 to 5 carbon atoms; and M is selected from the group consisting of hydrogen, alkali, alkaline earth metal, iron, copper, zinc, manganese, nickel, cobalt, mercury, ammonium, ethanolammonium, dimethylammonium; diethylammonium and diisopropylammonium; and n is an integer equal to the valency of M; in an agriculturally acceptable carrier.

2. The composition as claimed in claim 1, wherein said compound is at least one of the following compounds:

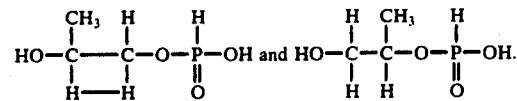

3. The composition as claimed in claim 1, wherein said compound is a mixture of the following:

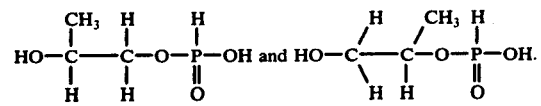

4. The composition as claimed in claim 1, wherein they additionally contain a fungicidally effective amount of the fungicide folpet.

5. The composition as claimed in claim 1, wherein they additionally contain a fungicidally effective amount of the fungicide captafol.

6. The composition as claimed in claim 1, wherein they additionally contain a fungicidally effective amount of the fungicide captan.

7. The composition as claimed in claim 1, wherein they additionally contain a fungicidally effective amount of the fungicide maneb.

8. The composition as claimed in claim 1, wherein they additionally contain a fungicidally effective amount of the fungicide benomyl.

9. The fungicidal composition as claimed in claim 1, wherein they additionally contain a fungicidally effective amount of the fungicide methyl N-2-benzimidazole carbamate.

10. A process for controlling fungus disease in plants, comprising applying to the plant or its environs a fungicidal effective amount of a composition as claimed in claim 1 for the preventive or curative treatment of plants subject to fungus disease.

* * * * *